United States Patent [19]
Farris

[11] Patent Number: 6,066,174
[45] Date of Patent: May 23, 2000

[54] IMPLANT INSERTION DEVICE

[75] Inventor: Robert A. Farris, Memphis, Tenn.

[73] Assignee: SDGI Holdings, Inc., Wilmington, Del.

[21] Appl. No.: 09/118,420

[22] Filed: Jul. 17, 1998

Related U.S. Application Data

[63] Continuation of application No. 08/677,794, Jul. 10, 1996, Pat. No. 5,782,830, which is a continuation-in-part of application No. 08/603,675, Feb. 20, 1996, abandoned, which is a continuation-in-part of application No. 08/543,563, Oct. 16, 1995, abandoned.

[51] Int. Cl.[7] .............................. A61F 2/44; A61B 17/28
[52] U.S. Cl. ............................................. 623/17; 606/206
[58] Field of Search ..................................... 606/205, 206, 606/140; 623/17

[56] References Cited

U.S. PATENT DOCUMENTS

| | | |
|---|---|---|
| D. 331,625 | 12/1992 | Price et al. . |
| 2,549,731 | 4/1951 | Wattley ..................................... 606/206 |
| 3,848,601 | 11/1974 | Ma et al. . |
| 4,877,020 | 10/1989 | Vich . |
| 5,222,973 | 6/1993 | Sharpe et al. ........................... 606/206 |
| 5,397,364 | 3/1995 | Kozak et al. . |
| 5,423,855 | 6/1995 | Marienne . |
| 5,843,121 | 12/1998 | Yoon ....................................... 606/206 |

OTHER PUBLICATIONS

Article entitled "Laparoscopic Bone Dowel Surgical Technique" by Sofamor Danek, the Spine Specialist, Memphis, Tennessee, 1995.

*Primary Examiner*—David J. Isabella
*Attorney, Agent, or Firm*—Woodard, Emhardt, Naughton Moriarty & McNett

[57] ABSTRACT

One embodiment of an implant insertion device includes a handle, a shaft having a proximal end attached to the handle and a distal end and a pair of jaws each having a first end attached to the distal end of the shaft, a free second end and a gripping element at the second end. The free ends of the jaws are movable between gripping positions to grasp the implant between the gripping elements and releasing positions to release the implant. The jaws are biased apart to the releasing positions. Each of the gripping elements defines a substantially uniform or flat gripping surface. In some embodiments the gripping surfaces include teeth. The gripping surfaces face one another to contact the surface of the implant when the jaws are in the gripping positions. The devices of this invention also include a hollow sleeve slidably disposed over the jaws for forcing the jaws together towards the gripping positions.

10 Claims, 6 Drawing Sheets

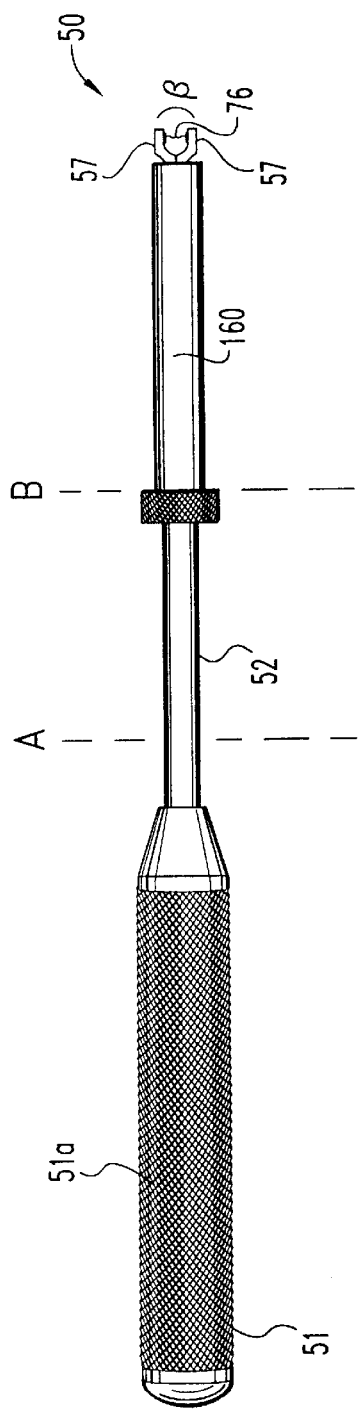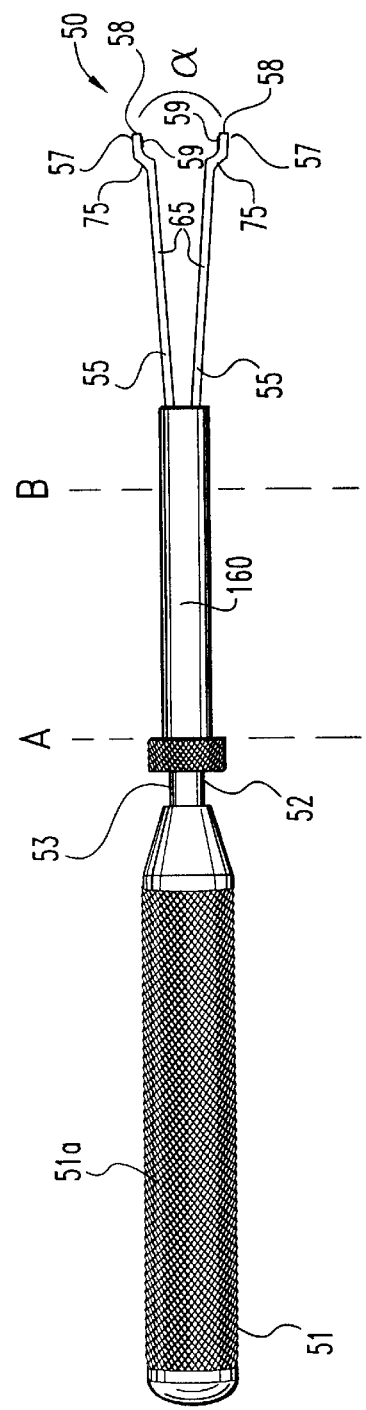
*Fig. 7*
*Fig. 8*

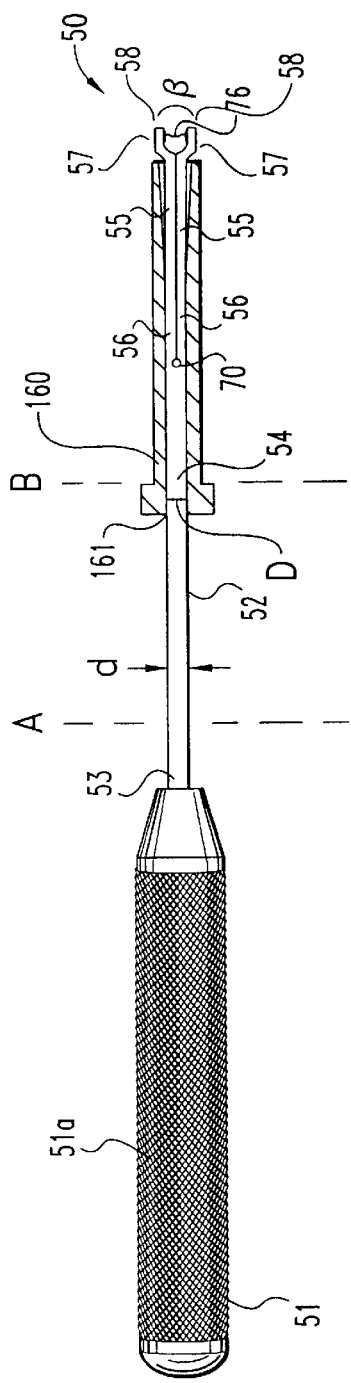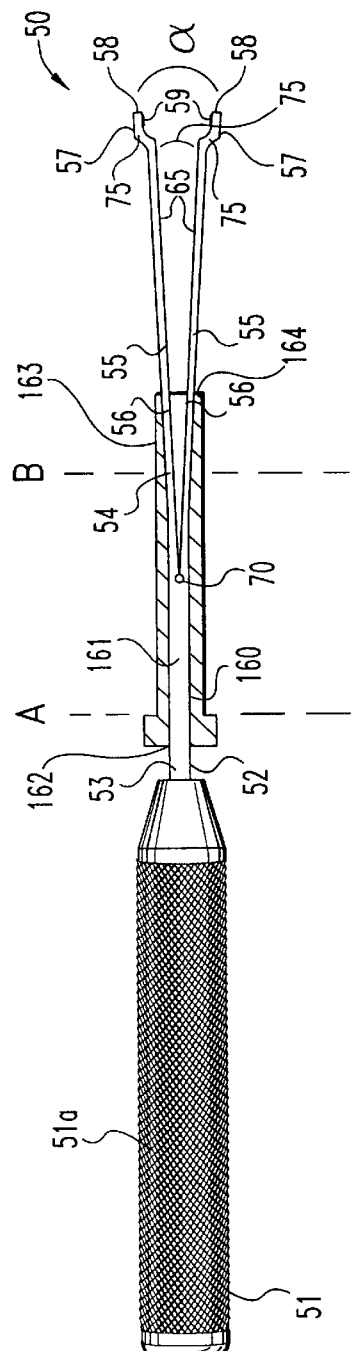
Fig. 9
Fig. 10

IMPLANT INSERTION DEVICE

This is a continuation patent application of patent application Ser. No. 08/677,794, filed Jul. 10, 1996 and issued Jul. 21, 1998 as U.S. Pat. No. 5,782,830, which is a continuation-in-part of application Ser. No. 08/603,675, filed Feb. 20, 1996, now abandoned, which is continuation-in-part of application Ser. No. 08/543,563, filed Oct. 16, 1995, now abandoned.

FIELD OF THE INVENTION

The present invention concerns intervertebral implants and implant insertion devices for implanting spacers, graft material and graft substitutes between vertebrae for stabilizing the spine.

BACKGROUND OF THE INVENTION

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs may be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain.

Bone grafts are often used to fill the intervertebral space to prevent disc space collapse and promote fusion of the adjacent vertebrae across the disc space. For example, in the Smith-Robinson technique for cervical fusion, the surgeon prepares the endplates of the adjacent vertebral bodies to accept a graft after the disc has been removed. The endplates are generally prepared to be parallel surfaces with a high speed burr. The surgeon sculpts the graft to fit tightly between the bone surfaces so that the graft is held by compression between the vertebral bodies. The bone graft is intended to provide structural support and promote bone ingrowth to achieve a solid fusion of the affected joint.

Unfortunately, the use of bone grafts presents several disadvantages. Autografts, bone material surgically removed from the patient, can be undesirable because they may not yield a sufficient quantity of graft material. The additional surgery to extract the autograft also increases the risk of infection and blood loss. The structural integrity at the donor site can be reduced. Furthermore, some patients complain that the graft harvesting surgery is more painful than the fusion surgery.

Allograft material, which is obtained from donors of the same species, is more readily obtained. However, allografts can be disadvantageous because of disease transmission, immune reactions and religious objections. Furthermore, allogenic bone does not have the osteoinductive potential of autogenous bone and therefore may provide only temporary support.

Both allograft and autograft present additional difficulties. Graft alone may not provide the stability required to withstand spinal loads. Internal fixation can address this problem but presents its own disadvantages such as the need for more complex surgery. Also, the surgeon is often required to repeatedly trim the graft material to obtain the correct size to fill and stabilize the disc space. This trial and error approach increases the length of time required for surgery. Furthermore, the graft material usually has a smooth surface which does not provide a good friction fit between the adjacent vertebrae. Slippage of the graft may cause neural and vascular injury, as well as collapse of the disc space.

Prosthetic implants can be used to prevent collapse of the disc space. The implant must provide temporary support and allow bone ingrowth. Success of the discectomy and fusion procedure requires the development of a contiguous growth of bone to create a solid mass because the implant may not withstand the compressive loads on the spine for the life of the patient.

Many attempts to restore the intervertebral disc space after removal of the disc have relied on metal devices. U.S. Pat. No. 4,878,915 to Brantigan teaches a solid metal plug. U.S. Pat. Nos. 5,044,104; 5,026,373 and 4,961,740 to Ray; 5,015,247 to Michelson and U.S. Pat. No. 4,820,305 to Harms et al., U.S. Pat. No. 5,147,402 to Bohler et al. and 5,192,327 to Brantigan teach hollow metal cage structures. Unfortunately, there are several disadvantages associated with the use of these metal implants. For example, metal implants may stress shield the bone graft, increasing the time required for fusion to occur.

Most of the prior implants do not adequately address the need for obtaining a solid fusion. Solid body metal implants do not allow bone ingrowth which may lead to the eventual failure of the implant. Surface porosity in such solid implants may not correct this problem because it often will not allow sufficient ingrowth to provide a solid bone mass strong enough to withstand the loads of the spine. On the other hand, the hollow cage structures of Harms, Ray, Michelson, Bohler and Brantigen allow ingrowth. These devices can also be filled with bone graft material to promote bone growth needed for solid fusion. However, the large openings disclosed in these references, while allowing bone ingrowth, reduce the amount of metal providing structural support, which can limit the implant's load bearing capability until fusion occurs.

Unfortunately, many of these metal devices are also difficult to machine and therefore expensive. For example, the superior and inferior surfaces of Brantigan (U.S. Pat. No. 5,192,327) define ridges for interdigitation with adjacent implants for stacking and biting into the endplates of adjoining vertebrae. Bohler (U.S. Pat. No. 5,147,402) discloses that the surface of the implant can be roughened to promote fusion. These features require more expensive machining and may also compromise the strength of the implant. Moreover the structure of these types of implants do not readily lend themselves for manufacture in smaller sizes for use in the cervical spine.

SUMMARY OF THE INVENTION

In accordance with one aspect of the invention, implant insertion devices are provided for inserting implants such as graft, graft substitutes and intervertebral spacers between vertebrae. A device according to this invention include: a handle, a shaft having a proximal end attached to the handle and a distal end and a pair of jaws each having a first end attached to the distal end of the shaft, a free second end and a gripping element at the second end. The free ends of the jaws are movable between gripping positions to grasp the implant between the gripping elements and releasing positions to release the implant. The first ends of the jaws form a first angle in the releasing positions and a smaller second angle in the gripping positions. The jaws can be biased apart to the releasing positions. Each of the gripping elements define a substantially uniform or flat gripping surface. The gripping surfaces face one another to contact only the surface of the implant when the jaws are in the gripping positions.

The devices of this invention also include forcing means for forcing the jaws together towards the gripping positions. In one aspect, the forcing means can include an actuator such as a hollow sleeve slidably mounted on the shaft and defining an inner bore for receiving the shaft and the first ends of said jaws. The sleeve is slidable between a first position adjacent the handle and a second engaging position spaced from the first position in a location between the first position and the free ends of the jaws. The sleeve forces the jaws together when the sleeve is in the engaging position.

In some embodiments, the gripping surfaces include teeth which contact the surface of the implant. In other embodiments, each of the jaws include a bend at the free end, each bend defining a platform for the implant when the jaws are in the gripping positions. Some embodiments of this invention also include a resilient joint between the first ends of the jaws. The jaws each include an elongate arm made of a resilient material. In some embodiments the joint includes a notch defined in the shaft.

One object of the invention is to provide devices for inserting implants such as graft, graft substitute and intervertebral spacers into spaces between vertebrae.

One benefit of the present invention is that it provides devices for inserting implants into intervertebral spaces which engage only the surface of the implant. The inserters of this invention have gripping surfaces which are substantially uniform or flat so that the gripping surfaces engage the implant only at the surface of the implant without violating the integrity of the surface of the implant.

Further, the devices of this invention do not require apertures or holes in the implant and so can be used to implant virtually any intervertebral implant. Other objects and further benefits of the present invention will become apparent to persons of ordinary skill in the art from the following written description and accompanying figures.

BRIEF DESCRIPTION OF THE DRAWINGS

FIG. 7 is a front elevational view of an inserter device which may be used to implant prosthetic devices and bone graft material.

FIG. 8 is a front elevational view of the device of FIG. 7 with the jaws in the releasing position.

FIG. 9 is a partial cross-sectional view of the device shown in FIG. 7.

FIG. 10 is a partial cross-sectional view of the device shown in FIG. 8.

DESCRIPTION OF THE PREFERRED EMBODIMENT

Figure 1:
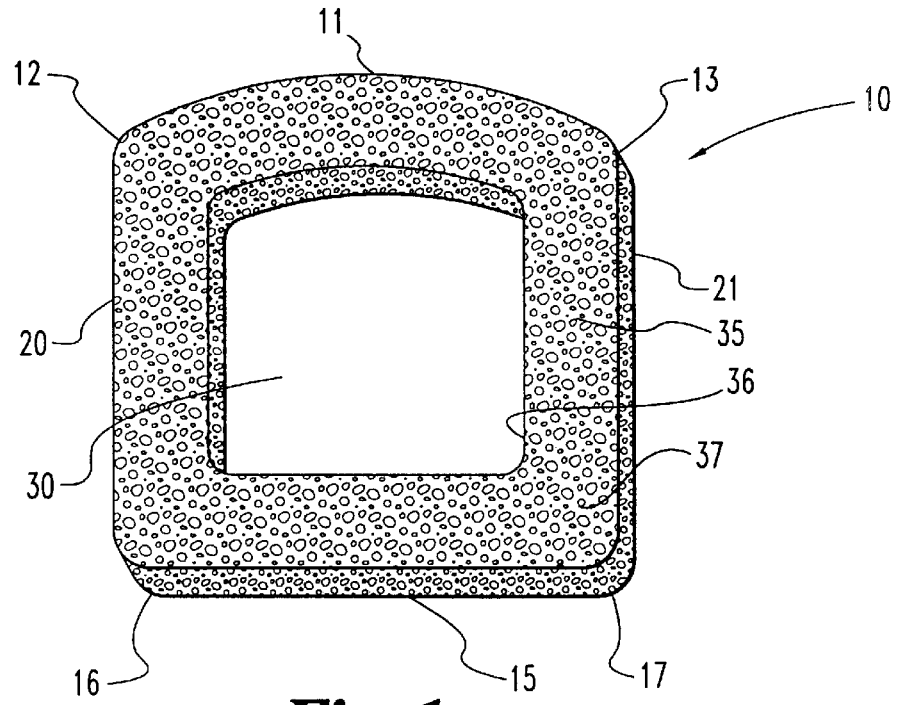
FIG. 1 is a top elevational view of the spinal implant according to one embodiment of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

This invention provides implant insertion devices for inserting graft, graft substitute or intervertebral spacers between vertebrae. The inserters engage to the lateral surface of the implant and do not require excessive distraction of the vertebrae because the inserters do not increase the insertion height of the implant. The gripping surfaces of the devices of this invention are substantially flat or uniform and do not violate the integrity of the implant nor do they require holes or apertures defined in the implant as do many prior art devices.

The present invention also provides spinal spacers for engagement between vertebrae. Spacers of this invention are made of a preferred biocompatible bone ingrowth material having interconnected continuous pores that provide a structure for bone ingrowth which resembles the natural porosity of bone. This material allows manufacture of smooth-shaped spacers which provide a friction fit with the adjacent vertebrae by virtue of the inherent properties of the material. This friction fit resists expulsion of the implant and may eliminate the need for internal fixation. The inventive implants restore the intervertebral disc space, provide a large surface area for bone growth and eliminate the need for invasive autograft harvesting and trial and error trimming of graft material to fit the intradiscal spaces. Implants according to this invention provide immediate load bearing capability and support for the vertebral column without stress shielding the bone implant material.

Figure 2:
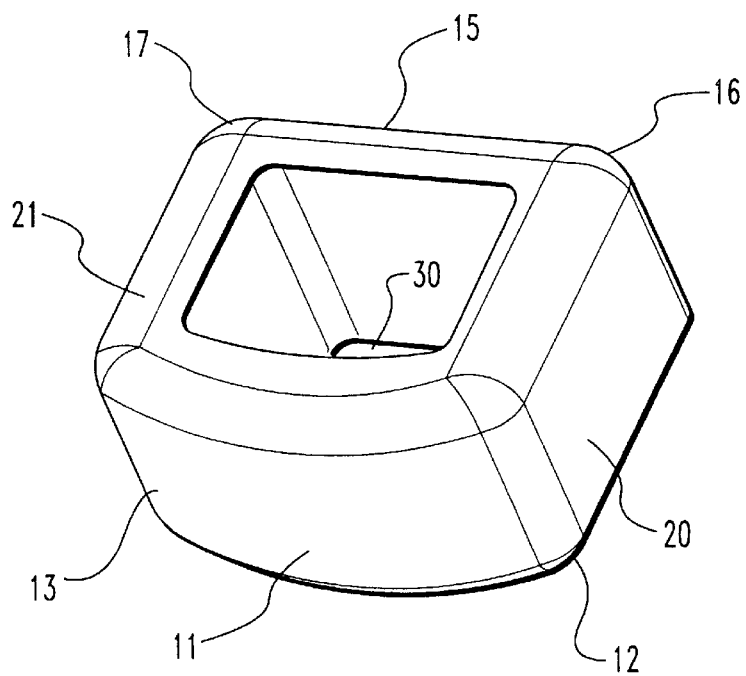
FIG. 2 is a top perspective view of an implant of this invention.
Figure 3:
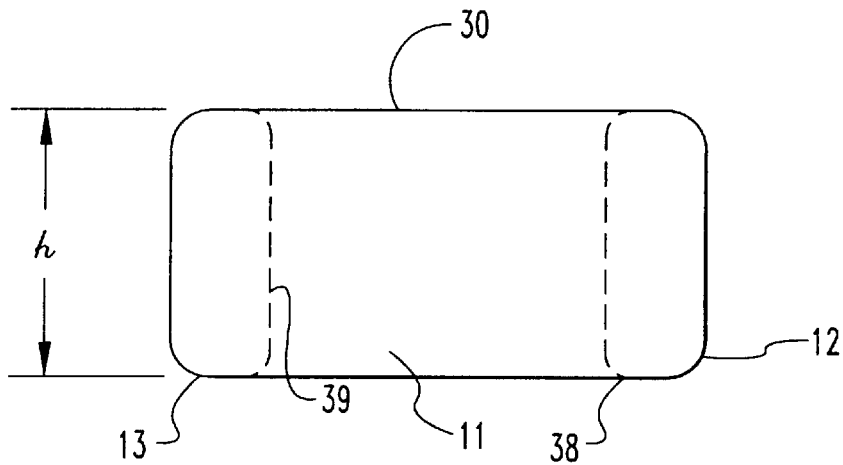
FIG. 3 is a front elevational view of the anterior end of the spacer depicted in FIG. 2.

A spacer 10 for engagement between the vertebrae in accordance with a preferred embodiment of the present invention is depicted in FIGS. 1–3. The spacer 10 includes an anterior wall 11 having opposite ends 12, 13, a posterior wall 15 having opposite ends 16, 17 and two lateral walls 20, 21. Each of the lateral walls 20, 21 is connected between the opposite ends 12, 13, 16, 17 of the anterior 11 and posterior 15 walls to define a chamber 30. The walls also include the superior face 35 which defines a first opening 36 in communication with the chamber 30. The superior face 35 includes a first friction or vertebral engaging surface 37. As shown in FIG. 3, the walls further include an opposite inferior face 38 defining a second opening 39 which is in communication with the chamber 30. The chamber 30 is preferably sized to receive osteogenic material to facilitate bone growth. The inferior face 38 includes a second friction or second vertebral engaging surface (not shown) which is similar to or identical to the first friction or vertebral engaging surface 37.

In one specific embodiment for an intervertebral disc replacement implant, a hollow D-shaped spinal spacer is provided. The anterior wall 11 as shown in FIGS. 1–3 is convexly curved. This anterior curvature is preferred to conform to the geometry of the adjacent vertebral bone and specifically to the harder cortical bone of the vertebrae. The D-shape of the spacer 10 also prevents projection of the anterior wall 11 outside the anterior aspect of the disc space, which can be particularly important for spacers implanted in the cervical spine.

Figure 4:
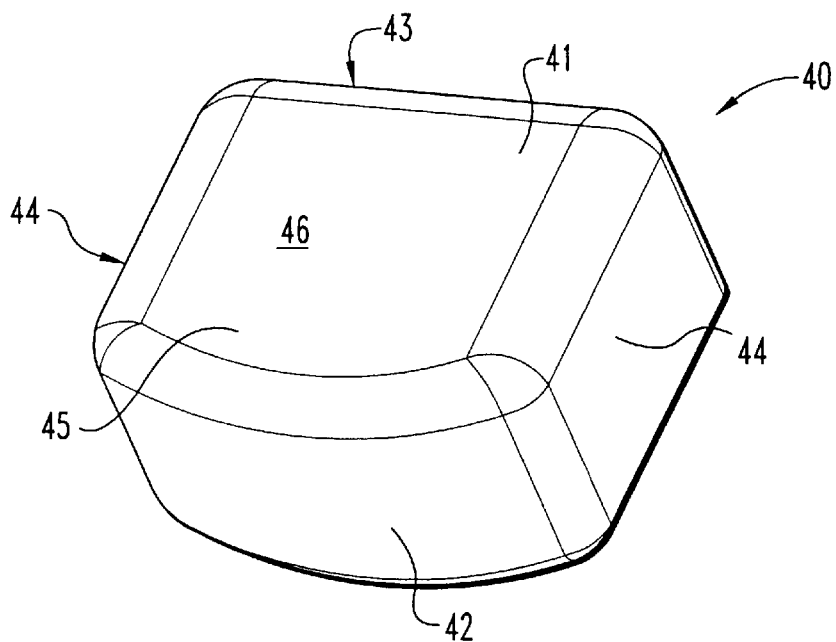
FIG. 4 is a top perspective view of a solid spacer of this invention.
Figure 5:
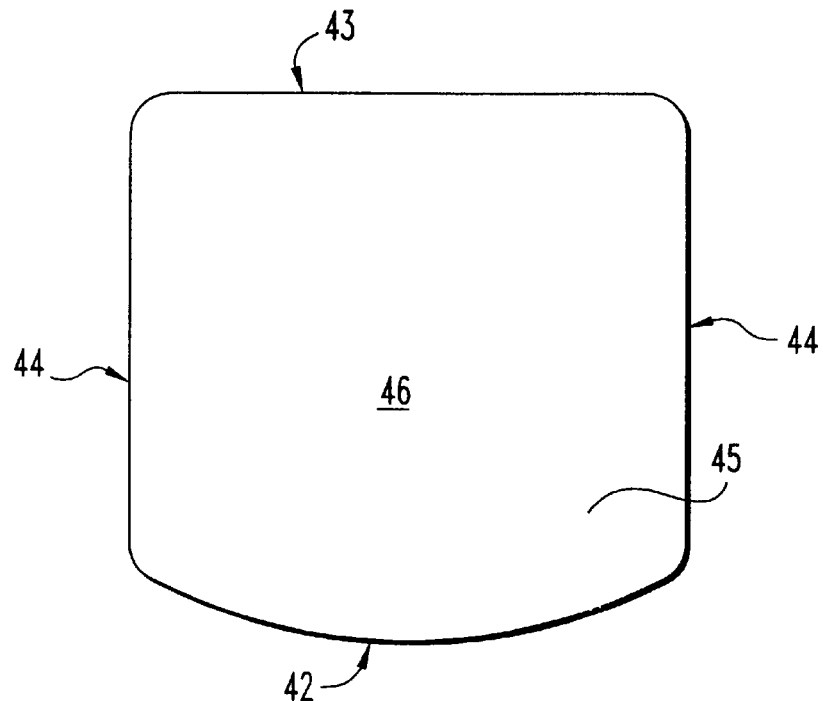
FIG. 5 is a top elevational view of the spacer shown in FIG. 4.
Figure 6:
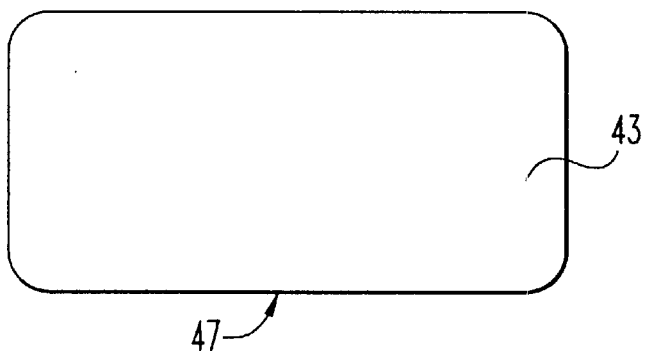
FIG. 6 is an end elevational view of the posterior end of the spacer shown in FIG. 4.
Figure 11:
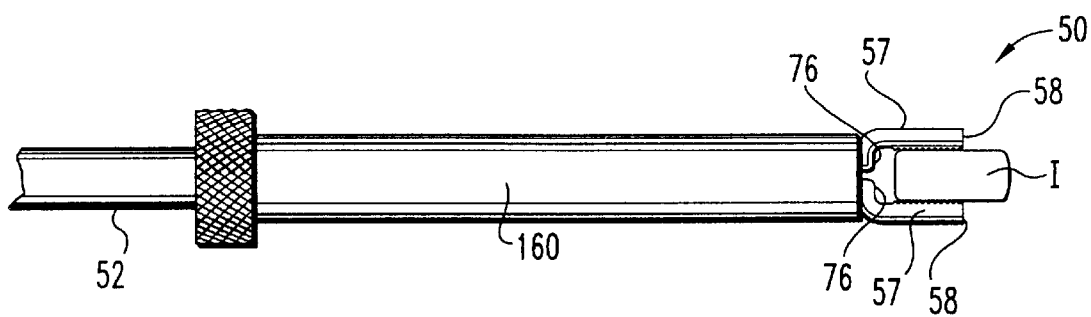
FIG. 11 is a front elevational view of a portion of the device depicted in FIGS. 7–11 gripping an implant for insertion.

Another embodiment in accordance with the principles of this invention is depicted in FIGS. 4–6. In this embodiment for a spinal prosthesis for engagement between vertebrae, a spacer 40 is provided which includes a spacer body 41 composed of a biocompatible bone ingrowth material having interconnected, continuous pores. The body 41 includes an anterior face 42 and a posterior face 43 which is spaced apart from and opposing the anterior face 42. The body 41 also includes two spaced apart and opposing lateral faces 44. A superior face 45 defining a first vertebral engaging surface 46 is spaced apart from and opposing an inferior face 47. The inferior face 47 defines a second vertebral engaging surface (not shown).

Preferably, the anterior face 42 of the spacer 41 is convexly curved and the posterior face 43 is flat to form a solid D-shape block. The solid block embodiment 40 provides more surface area for bone ingrowth and more load bearing area than the spacers 10 that include a chamber 30. The ingrowth material of the body 41 eliminates some of the concerns normally associated with a solid metal spacer such as stress shielding and pseudoarthrosis. The interconnected, continuous pores provide a scaffold for contiguous bone growth. This characteristic enables a solid body design without compromising the success of the fusion.

The spacers 10, 40 of this invention are preferably shaped to be conveniently incorporated into current surgical techniques. For example, a flat posterior wall 15 or face 43, as shown in FIGS. 4–6, can be easily incorporated into Smith Robinson surgical fusion technique. See, for example, Smith, M.D., G. W. and R. A. Robinson, M.D., "The Treatment of Certain Cervical-Spine Disorders By Anterior Removal Of The Intervertebral Disc And Interbody Fusion", *J. Bone And Joint Surgery*, 40-A:607–624 (1958) and Cloward, M.D., R. B., "The Anterior Approach For Removal Of Ruptured Cervical Disks", in meeting of the Harvey Cushing Society, Washington, D.C., Apr. 22, 1958. After partial or total discectomy and distraction of the vertebral space, the surgeon prepares the end plates for the spacer 10, 40 preferably to create flat posterior and lateral edges. The spacer 10, 40 fits snugly with its flat surfaces against the posterior and lateral edges which prevents medial and lateral motion of the spacer 10, 40 into vertebral arteries and nerves. This also advantageously reduces the time required for the surgery by eliminating the trial and error approach to achieving a good fit with bone grafts. Normally, the surgeon is required to repeatedly whittle away the graft to obtain the correct size to fit in the intervertebral space.

Advantageously, the intervertebral spacers of the present invention may not require internal fixation. The spacers are contained by the compressive forces of the surrounding ligaments and muscles, and the disc annulus if it has not been completely removed. Temporary external immobilization and support of the instrumented and adjacent vertebral levels is generally recommended until adequate fusion is achieved. For example, a cervical collar is recommended when the spacer is implanted in the cervical spine.

The spacers 10, 40 of this invention are preferably composed of a biocompatible bone ingrowth material having interconnected continuous pores throughout the body of the spacer. Any suitable material is contemplated which has a compressive endurance (at five million cycles) of at least 100 pounds and a compressive strength of at least about 350 pounds. Most preferably the bone ingrowth material is a biocompatible composite which includes a non-metallic rigid foam substrate formed by an interconnected network of carbonaceous material defining continuous, interconnected pores and a metallic film substantially covering the interconnected network. Such materials are described in U.S. Pat. No. 5,282,861 to Kaplan which is herein incorporated by reference. The metallic film preferably includes a Group VB transition metal such as tantalum, niobium or alloys thereof. Tantalum is most preferred because it is thought to be the most biocompatible, corrosion resistant metal for providing structure. Most preferably, the rigid foam substrate is carbon and the metallic material is tantalum which is deposited onto the carbon foam substrate with chemical vapor infiltration as described in Kaplan. This material is available from Implex Corp., 80 Commerce Drive, Allendale, N.J. 07401-1600 and is marketed under the name Hedrocel®.

The spacers of this invention can be manufactured according to the methods described in the Kaplan 5,282,861 Patent. Alternatively, spacers can be machined from composite blocks obtained from Implex Corp., and then preferably resealed. Resealing refers to the process whereby metal is redeposited onto the carbonaceous foam material that became exposed by the machining process. Any suitable machining method which will not smear the pores of the material, such as hot wire EDM, is contemplated.

Kaplan type materials provide three important advantages: complete porosity, roughness and strength. As discussed in the Kaplan patent, the open cell tantalum material provides highly interconnected three-dimensional porosity that encourages bone ingrowth. Kaplan type materials facilitate bone ingrowth throughout the entire device for complete fusion and have the strength of metal without the disadvantages of metal such as stress shielding and incomplete fusion. Because the material of the spacers 10, 40 itself is porous and supports bone ingrowth, there is no need for extra machining of open side slots. An additional benefit of the porosity of these materials is that a bone growth inducing composition can be introduced into the pores. For example, in one embodiment, the composition includes a bone morphogenic protein in a liquid carrier which can be injected into the pores to promote fusion. These materials also provide an unexpected benefit in that the roughness of the surface provides a friction fit between the vertebral bodies. Inherent properties of the tantalum foam material provide stability which other prior devices obtain through extra machining of teeth and ridges. The roughness features which must be machined into these prior devices may also compromise strength. Advantageously, the preferred material allows spacers of the present invention to be manufactured with a flat geometry with or without an open chamber 30.

Spacers according to this invention which are composed of a tantalum foam composite are less likely to slip than bone graft or smooth design implants due to the roughness properties of the material. Spacers 10, 40 which incorporate the tantalum open cell structure or similar biomaterials preferably have a surface roughness of at least 1 micron RMS and preferably at least about 2 microns RMS. The spacers 10, 40 may also preferably have a surface roughness of about 10 microns RMS. It has been found that these surface roughness values are sufficient to resist expulsion of the spacers under normal spinal loads.

Any biocompatible material which is highly porous and can withstand high spinal loads is contemplated. Most preferably, the biocompatible material will have surface roughness or friction properties similar to the tantalum foam material described above. The preferred material is preferably about 75–85 percent porous. The pores are defined by struts or structural members which preferably range from about 50 to about 150 microns in diameters. The thickness of the struts depends on relative porosity. The preferred material of the present invention defines at least about 10–20 pores per inch (ppi) preferably 60–65 ppi and most preferably 80 ppi. Strength tests have shown that 80 ppi is stronger than material with lower ppi values because more tantalum foam matrix is provided. The strength of lower porosity materials can be increased by increasing the thickness of the metallic film. For cervical spacers, the relative density of the material is preferably between about 10% to about 30%. Most preferably the relative density is between about 16 to about 25%. The relative density for lumbar applications may be higher. The material is manufactured to have a mean pore size which is conducive to bone ingrowth, preferably between about 200 microns to about 850 microns and most preferably a mean pore size of about 400 or 520 microns. The pore size of 60 ppi is about 850 microns. The pore size of 80 ppi is about 520 microns. It is understood that pore size and porosity is controlled in the manufacturing process.

During a surgical implantation procedure, the surgeon may apply an osteogenic material to the device by packing the chamber 30 with an osteogenic material or by introducing an osteogenic composition to the pores of the bone ingrowth material. Any suitable osteogenic material or composition is contemplated. For example, the osteogenic material may include osteoconductive materials such as allograft or certain bioceramics. Allograft materials may include morcellized bone graft from a bone bank. The osteogenic material preferably is an osteoinductive material such as autograft, certain bioceramics or osteoinductive proteins. Autograft may be taken from the iliac crest or may include osteocytes or other bone reamed away by the surgeon while preparing the end plates for the spacer. Bioceramics may include biphasic calcium phosphate ceramics such as hydroxyapatite/tricalcium phosphate ceramics which are well known in the art. The osteogenic compositions may comprise a therapeutically effective amount of a bone inductive factor such as a bone morphogenic protein in a pharmaceutically acceptable carrier.

Advantageously, where graft is chosen as the osteogenic material, only a very small amount of bone material is needed to pack the chamber 30. The graft itself is not required to provide structural support as this is provided by the spacer 10. Instead the graft is merely required for its osteoconductive and/or osteoinductive properties to promote fusion across the disc space. The donor surgery for such a small amount of bone is less invasive and better tolerated by the patient. There is usually little need for muscle dissection in obtaining such small amounts of bone. The present invention therefore eliminates many of the disadvantages of autograft.

For the osteogenic compositions, any suitable carrier which provides a vehicle for introducing the osteogenic material into the pores of the bone ingrowth material or the chamber 30 of the spacer 10 is contemplated. Such carriers are well known and commercially available. One preferred carrier is an absorbable collagen sponge marketed by Integra LifeSciences Corporation under the trade name Helistat® Absorbable Collagen Hemostatic Agent. Another preferred carrier is an open cell polylactic acid polymer (OPLA). Other potential matrices for the compositions may be biodegradable and chemically defined calcium sulfate, tricalcium phosphate (TCP), hydroxyapatite (HA), biphasic TCP/HA ceramic, polylactic acids and polyanhydrides. Other potential materials are biodegradable and biologically well defined, such as bone or dermal collagen. Further matrices are comprised of pure proteins or extracellular matrix components. The osteoinductive material may also be an admixture of the osteoinductive cytokine and a polymeric acrylic ester carrier. The polymeric acrylic ester can be polymethylmethacrylic. The carriers are preferably provided in strips or sheets which may be folded to conform to the chamber 30.

The choice of carrier is based on biocompatibility, biodegradability, mechanical properties and interface properties. The particular application of the compositions of the invention will define the appropriate formulation. The carrier may be any suitable carrier capable of delivering the proteins to the spacer.

Bone morphogenic proteins (BMPs) have been found to significantly decrease the time required to achieve fusion across an instrumented disc space. BMPs may be isolated and purified from bone or genetically engineered BMPs. Most preferably, the bone morphogenic protein is a BMP-2, such as recombinant human BMP-2. However, any bone morphogenic protein is contemplated including but not limited to bone morphogenetic proteins designated as BMP-1 through BMP-13. Such BMPs are available from Genetics Institute, Inc., of Cambridge, Mass., and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al which are hereby incorporated by reference.

The BMP may be provided in freeze-dried form and reconstituted in sterile water or another suitable carrier. The carrier may be any suitable medium capable of delivering the proteins to the implant. Preferably the medium is supplemented with a buffer solution as is known in the art. In one specific embodiment of the invention, BMP-2 is suspended or admixed in a liquid carrier, such as water or liquid collagen. The liquid can be dripped onto the spacers 10, 40 or the spacers can be immersed in a suitable quantity of the liquid, in either case for a period of time sufficient to allow the liquid to invade all of the interconnected pores throughout the spacer body.

In some cases, prior to introduction of the BMP, a BMP bonding agent is applied to the porous spacer 10, 40 so that the agent can coat the surface of the pores in the spacer body. Preferably, the agent is a calcium phosphate composition. It has been discovered that the rate of delivery of bone morphogenic proteins to the fusion site can be controlled by the use of such agents. The calcium phosphate compositions are thought to bond with the bone morphogenic protein and prevent the BMP from prematurely dissipating from the device before fusion can occur. It is further believed that retention of the BMP by the agent permits the BMP to leach out of the device at a rate that is conducive to complete and rapid bone formation and ultimately, fusion across the disc space. Any suitable, biocompatible calcium phosphate composition is contemplated. In a preferred embodiment, a layer of hydroxyapatite several microns thick is applied to the Kaplan material. The hydroxyapatite covers the tantalum film-covered ligaments while leaving the pores open. Also contemplated are tricalcium phosphate ceramics and hydroxyapatite/tricalcium phosphate ceramics.

The calcium phosphate composition may be applied to the porous biocompatible material of the implant in any suitable manner such as plasma spraying and chemical dipping where the porous material is dipped into a slurry of calcium phosphate composition. Methods for applying a coating of calcium phosphate compositions are described in the following: U.S. Pat. No. 5,164,187 to Constantz et al., U.S. Pat. No. 5,1656,058 to Wang et al., U.S. Pat. No. 5,030,474 to Saita et al, U.S. Pat. No. 5,318,898 to Israel, U.S. Pat. No. 5,330,826 to Taylor et al, U.S. Pat. No. 5,128,169 to Saita et al, U.S. Pat. No. Re. 34,037 to Inoue et al, U.S. Pat. No. 5,068,122 to Kokubo et al, and U.S. Pat. Nos. 5,188,670 and 5,279,831 to Constantz which are hereby incorporated by reference.

Spacers according to the present invention have compressive endurance and strengths sufficient to withstand the normal loads of the spinal column. Spacers of the present invention preferably have a compressive endurance of at least 100 pounds out to 5 million cycles. Most preferably spacers of the present invention have a compressive endurance of about 500 pounds. Spacers of the present invention also preferably have compressive strengths which are greater than reported bone graft values of between 175 and 1,140 pounds. Spacers of the present invention preferably have compressive strengths of at least 350 pounds, and most preferably about 1,500 pounds.

Any suitably sized spacer is contemplated. In one specific embodiment an interbody fusion spacer according to this invention is contemplated. Preferably, the spacers 10, 40 have a height h (FIG. 3) approximating the height of a particular human disc space, such as the cervical spine. In some applications, it may be preferable that the height of the spacer 10, 40 be slightly larger than the height of a human disc space to preserve disc space height under the compressive forces of the spine and to avoid the effects of bone erosion. In one specific embodiment, a cervical spacer has a height of about 7 mm, a width of about 14 mm and a length (anterior to posterior) of about 14 mm. In another specific embodiment, the spacer has a width and length of about 11 mm and a height of between 7 and 14 mm. The invention contemplates that the walls of the spacer will be of sufficient thickness to provide structural support. In one specific embodiment for use in a cervical spine, the walls are each about 2 mm thick. Appropriately sized thoracic and lumbar spacers are also contemplated to be used with appropriate surgical techniques.

Implants according to this invention combine the advantages of porous biocompatible materials with stronger materials such as metals. The implants provide immediate load bearing capability without stress shielding. The porous biocompatible material provides a large surface area for bone ingrowth and eliminates the need for invasive autograft. Devices of this invention reduce surgical time by avoiding the need for trial and error trimming of graft material to fit the intradiscal space. The biocompatible material also preferably has a surface roughness that provides sufficient frictional properties to hold the spacer in place and avoid its ejection from the disc space. Spacers of the present invention can be efficiently and inexpensively manufactured.

The present invention further contemplates an inserter 50 as depicted in FIGS. 7–13 for facilitating the implantation of the spacers 10, 40 and other implants such as bone graft and bone graft substitute. The inserter 50 includes a handle 51 a shaft 52 having a proximal end 53 extending from the handle 51 and a distal end 54 with a pair of jaws 55 each attached to the distal end 54 of the handle 51. The handle 51 is preferably provided with knurlings 51a or other suitable patterns to enhance manual gripping of the handle.

Each of the jaws 55 has a first end 56 attached to the distal end 54 of the shaft 52 and a free second end 57. Each of the free ends 57 includes a gripping element 58 for engaging and gripping an implant. The free ends 57 of the jaws 55 are movable between gripping positions (FIGS. 8, 10 and 11) to grasp the implant between the gripping elements 58 and releasing positions (FIGS. 8 and 10) to release the implant I. The first ends 56 of the jaws 55 form a first angle $\alpha$ in the releasing positions and a smaller second angle $\beta$ in the gripping positions. The jaws 55 are preferably biased apart to the releasing positions due to their construction. In one embodiment a hole is drilled in the shaft 52 to form the joint 70 and the shaft 52 can be divided to the joint 70 with an electrified wire. The arms 65 can then be formed in their open position with a bending tool. Alternatively, the arms 65 can be attached in position to the shaft 52, such as by welding or other suitable means. The arms can be straight or curved. In a preferred embodiment, the jaws 55 are an integral part of the shaft 52 and are machined into shape. The jaws 55 include elongate arms 65 which are made of a rigid yet resilient material such as stainless steel. Alternatively the arms 65 can be separate from the shaft 52 but attached to the shaft 52 in a suitable manner. A resilient joint 70 can be provided between the arms 65. In the preferred embodiment depicted in FIGS. 7–13 the resilient joint is a notch defined in the shaft. Other resilent joint constructions or biasing members are contemplated that can keep the jaws apart to receive an implant.

In the fully closed or gripping position, the gripping elements, identified as 58 in FIG. 7, are separated by a distance sufficiently close to grip a hollow spacer or other implant I therebetween. In particular, the closed gripping elements 58 and can contact the side surfaces of the two lateral walls 20, 21 of the spacer 10. In one preferred embodiment, the gripping elements 58 include substantially uniform or flat gripping surfaces 59. The gripping surfaces 59 face one another to contact only the surface of the implant I when the jaws 55 are in the gripping positions. The uniform gripping surfaces 59 may be roughened or knurled to enhance the grip on the outside surface of the implant. In a most preferred embodiment, the gripping surfaces 59 include a plurality of teeth 60, such as saw teeth. In a most preferred embodiment, the saw teeth 60 each include a trailing surface that is angled back from the jaws 55 toward the handle 51.

Figure 12:
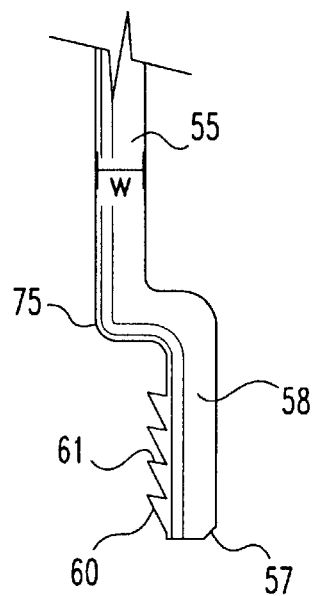
FIG. 12 is a front elevational view of the gripping element of the device depicted in FIG. 11.
Figure 13:
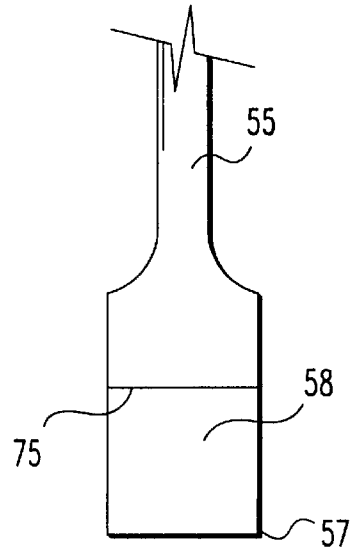
FIG. 13 is a side elevational view of the gripping element depicted in FIG. 12.

The jaws 55 also preferably include an offset 75 or a bend at the free end as best shown in FIG. 12. The offsets 75 define a platform 76 for the implant when the jaws are in the gripping positions. The platform more securely grasps the implant I during the insertion procedure and prevents the implant I from sliding back towards the joint 70 as the inserter 50 is operated to grip the implant I. In this embodiment the gripping elements 58 can be welded to the arms 56. Alternatively, the shaft 52, jaws 55 and gripping elements 58 can be machined from a single rod.

The inserter 50 further includes an actuator operable on the jaws 55 to force the jaws 55 together. In one embodiment, the actuator is a sleeve 160 that is concentrically disposed around and slidably mounted on the shaft 52. Preferably the sleeve 160 defines an inner bore 161 for receiving the shaft 52 and the first ends 56 of the jaws 55. The sleeve 160 is slidable between a first position A adjacent the handle 51 and a second engaging position B spaced from the first position A in a location between the first position A and the free ends 57 of the jaws 55.

The internal bore 161 includes with a first portion 162 having a dimension D slightly greater than the diameter d of shaft 52 and a flared portion 163 at its distal end 164. Preferably the inner dimension D of the bore 161 is substantially equal to twice the width W of each of the arms. The flared portion 163 defines the first angle α to accomodate the jaws 55 when the jaws 55 are in the releasing position A. In the preferred embodiment, when the jaws 55 are in their fully opened position, the jaws 55 contact the flared portion 163 of the bore 161.

In the use of the inserter 50, the sleeve 160 is slid along the shaft 52, and more particularly along the opened jaws 55, to push the jaws 55 together. As the jaws 55 are pushed together, the gripping surfaces 59 engage and firmly grip a spacer 10, 40 or implant I as described above. Advantageously this inserter can then be extended percutaneously or otherwise into the surgical site to implant a spacer 10, 40 in the intradiscal space. Once the spacer is properly positioned, the sleeve 160 can be moved back towards the handle 51 so that the two jaws 55 spread apart to the releasing positions A, thereby releasing the spacer 10, 40. The jaws 55 can spread apart due to their natural resilence or due to another biasing means as discussed above. The inserter 50 can then be withdrawn from the surgical site with the jaws fully opened, or the sleeve can be advanced along the shaft once the gripping surfaces 59 have cleared the spacer 10, 40.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An implant insertion device, comprising:
   a handle;
   a shaft having a proximal end and a distal end, said proximal end attached to said handle;
   a pair of jaws integrally formed with said shaft, each of said free ends including a gripping element, said free ends of said jaws movable between gripping positions to grasp the implant between said gripping elements and releasing positions to release the implant, said first ends of said jaws forming a first angle in said releasing positions and a smaller second angle in said gripping positions; and
   an actuator operable on said jaws to force said jaws together towards said gripping positions, said actuator includes a hollow sleeve slidably mounted on said shaft, said hollow sleeve having a proximal end and an opposite distal end, said hollow sleeve having a substantially uniform outer diameter between said proximal and distal ends, said hollow sleeve defining an inner bore for receiving said shaft and said first ends of said jaws, said sleeve slidable between a first position adjacent said handle and a second engaging position spaced from said first position in a location between said first position and said free ends of said jaws, said sleeve forcing said jaws together when said sleeve is in the engaging position,
   wherein a portion of said inner bore adjacent said jaws includes a flared portion, said flared portion defining said first angle to accommodate said jaws when said jaws are in said releasing position.

2. The device of claim 1 wherein each of said jaws includes a bend at said free end, each said bend defining a platform for the implant when said jaws are in said gripping positions.

3. The device of claim 1 further comprising a resilient joint between said first ends of said jaws, said jaws each including an elongate arm made of a resilient material.

4. The device of claim 3 wherein said joint includes a notch defined in said shaft.

5. The device of claim 1 wherein said handle includes a gripping surface defining knurlings for gripping the handle.

6. The device of claim 1 wherein said jaws each include an elongate arm between said first end and said gripping element, each said arm having a width and said bore having an inner dimension substantially equal to twice said width.

7. The device of claim 1 further comprising biasing means for biasing the jaws apart to said releasing position.

8. The device of claim 7 wherein said biasing means includes said jaws having elongate arms that are curved apart relative to each other.

9. The device of claim 7 wherein said biasing means includes a resilent hinge between said jaws.

10. The device of claim 7 wherein said biasing means includes said jaws having elongate arms that are formed apart relative to each other.

* * * * *